: US 6,517,862 B2
(45) Date of Patent: Feb. 11, 2003

(12) United States Patent
Burgard

(54) ACESULFAME-METAL COMPLEXES, PROCESS FOR THEIR PREPARATION AND THEIR USE

(75) Inventor: Andreas Burgard, Frankfurt am Main (DE)

(73) Assignee: Nutrinova Nutrition Specialties & Food Ingredients GmbH (DE)

( * ) Notice: Subject to any disclaimer, the term of this patent is extended or adjusted under 35 U.S.C. 154(b) by 0 days.

(21) Appl. No.: 09/811,203

(22) Filed: Mar. 16, 2001

(65) Prior Publication Data

US 2001/0041738 A1 Nov. 15, 2001

(30) Foreign Application Priority Data

Mar. 17, 2000 (DE) .......................................... 100 13 259

(51) Int. Cl.[7] ................................................ A61K 47/00
(52) U.S. Cl. ..................... 424/439; 424/400; 424/630; 424/639; 424/641; 424/646
(58) Field of Search .................................. 424/489, 400, 424/439, 630, 641, 639, 646

(56) References Cited

U.S. PATENT DOCUMENTS 6,156,332 A * 12/2000 Bakal et al. ................. 424/400

FOREIGN PATENT DOCUMENTS

EP 0 155 634 3/1985
WO WO 00/72701 A1 12/2000 ........... A23L/1/236

OTHER PUBLICATIONS

Beck, W et al. "*Palladium–undPlatin(II)–Komplexe mit den Anionen von–6–Methyl–1,2,3–oxathiazin–4(3H)–on–2, 2–dioxid und N–2–Pyrimidinylsulfanilamid*" *Chemische Berichte* Bd. 118, Nr. 2, 1985, Seiten 444–449 XP00204730.

* cited by examiner

Primary Examiner—Thurman K. Page
Assistant Examiner—Robert M. Joynes
(74) Attorney, Agent, or Firm—ProPat, L.L.C.

(57) ABSTRACT

Acesulfame-metal complexes, formed from a trace element, preferably Fe, Zn, Cu, Mn, Co and 2 molecules of acesulfamic acid by precipitation reaction with the use of suitable salts, are distinguished by a pleasantly sweet taste and are therefore suitable as sweeteners, food supplements and for enrichment of food, medicaments and feeds with trace elements.

14 Claims, No Drawings

ACESULFAME-METAL COMPLEXES, PROCESS FOR THEIR PREPARATION AND THEIR USE

BACKGROUND OF THE INVENTION

Some trace elements are important for normal bodily functions. In the event of deficiency symptoms, the targeted supply of trace elements beyond the amounts taken in with the customary diet is required or at least desirable. Deficiency symptoms of this type can occur in the case of malnutrition, but also in the case of disturbed absorption due to physical malfunctions. Sufficient supply with trace elements is important not only in the case of humans, but also in animal growth. Trace elements and their importance are described, for example, in Römpp Chemie Lexikon [Römpp's Chemistry Lexicon], 9th edition, under this headword. These trace elements include, in particular, iron, zinc, copper, manganese and cobalt.

However, it is a problem for sufficient supply of trace elements, in particular in the form of their salts, that many salts of these trace elements taste unpleasant, even in small amounts, and in particular have an astringent taste. Incorporation of compounds of these trace elements into suitable foods, medicaments or feeds and supply via specific preparations can therefore be difficult owing to lack of acceptance by humans and animals. Provision in a pleasant-tasting form would markedly improve the targeted application in foods, medicaments and feeds.

It has now been found that the known sweetener acesulfame (6-methyl-3,4-dihydro-1,2,3-oxathiazin-4-one 2,2-dioxide), which has hitherto only been offered as potassium salt (acesulfame-K) and of which salts with alkali metals and alkaline earth metals, for example sodium salts, potassium salts, magnesium salts and calcium salts, the acid-reacting acesulfame itself, which represents acesulfamic acid, and some amine salts are known, forms with these elements stable complexes, preferably with in each case two acesulfame anions per metal atom. These complexes are surprisingly distinguished by a pleasantly sweet taste from which the astringent note of many salts of these trace elements is absent.

BRIEF DESCRIPTION OF THE INVENTION

The present invention thus comprises complex compounds of the trace elements, preferably of the metallic trace elements, for example iron, copper, zinc, chromium, selenium, cobalt, molybdenum, silicon, manganese, nickel, vanadium and boron, in particular preferably zinc, copper, iron, manganese and cobalt, with acesulfame. These are preferably metal complexes of acesulfame which are composed of one trace element metal and 2 acesulfame molecules and which, in addition, if appropriate can contain water of crystallization. These are defined compounds of which the metal is present in the cationic form and the acesulfame molecules are present in the anionic form.

DETAILED DESCRIPTION OF THE INVENTION

By means of the fact that the trace elements or metal cations in these complexes are preferably bound as salts, they are bioavailable after solvolysis by water and can be absorbed as such by metabolism.

These complexes can be used without problems in the customary processing steps of foods and production of preparations for supplementing the diet, or used in medicaments and cosmetic compositions, for example toothcare and oralcare compositions or in feeds or as feed additives, for example in the form of a premix. Processing is simple and is performed by known methods. In the case of solid preparations, the inventive complexes are mixed in solid form, if appropriate in suitable particle size, with the other ingredients. For use in tablets, compressed compositions and comparable products and pulverulent preparations, they can be granulated together with other ingredients suitable for this and further processed as granules. Owing to their good solubility, however, they can also readily be used in liquid products from the said fields or processed in the form of their aqueous solutions.

The present invention thus also comprises the use of the inventive acesulfame-trace element complexes as food supplements or food additives and their use in medicaments, feeds or cosmetic compositions, for example toothcare or oralcare compositions, in any form suitable therefor, for example as solid preparations in the form of, for example tablets, capsules, compressed compositions, granules, solid premix, pulverulent preparations or as liquid preparations, for example solutions, preferably aqueous solutions or liquid premix.

Finally, the present invention also relates to a process for preparing the inventive complex compounds. The acesulfame or its potassium salt, acesulfame-K, serving as starting substance, are commercially available or can, as can other desired acesulfame salts, be prepared by the process described in EP-A 0 155 634.

To prepare these complexes a process is used by which other ionic constituents of the starting materials suitable for the preparation may be eliminated. This can be achieved either by separating off sparingly soluble compounds of the other ionic constituents or by using starting materials in which from the start only trace elements and acesulfame remain in a solution from which the complexes are isolated in a suitable manner. This process comprises reacting salts of acesulfame, whose cations form suitable sparingly soluble compounds which may be precipitated, in particular the calcium salt but also the barium salt of acesulfame, with soluble salts of the trace elements whose anions form sparingly soluble compounds with the cations of the acesulfame salt, for example sulfates or reacting basic carbonates of the trace elements with acesulfamic acid (acesulfame) with release of $CO_2$ in which precipitates formed in each case are if appropriate separated off before the desired acesulfame complexes are isolated. This isolation is preferably achieved by crystallization, for example by evaporation of the solvent, preferably water or water-miscible solvents, or by adding water-miscible solvents to the reaction mixture. Preferred water-miscible solvents are, for example alcohols.

The acesulfame salts serving as starting materials of the reaction can be introduced, for example, as aqueous solution or else formed in what is termed a one-pot reaction from acesulfame and a suitable alkaline earth metal carbonate (Ba, Ca salt) before addition of the trace element salt.

The invention is described in more detail by the examples below without thereby restricting its extent:

The invention is described by the following examples:

EXAMPLE 1

Acesulfame-zinc Complex

Method 1

20 mmol (3.947 g) of sparingly soluble barium carbonate (or 20 mmol of calcium carbonate) are introduced into 20 ml of water and 40 mmol (6.525 g) of acesulfame-H are added. After $CO_2$ formation has ended, a homogeneous solution is obtained from which sparingly soluble barium sulfate (or calcium sulfate) is precipitated out by 20 mmol (0.575 g) of zinc(II) sulfate heptahydrate. After filtering off the precipitate and concentrating the solution, the acesulfame-zinc complex crystallizes out in the form of colorless crystals with 97% yield.

Method 2

10 mmol (3.42 g) of sparingly soluble basic zinc carbonate hydrate ($ZnCO_3 \cdot 2Zn(OH)_2 \cdot H_2O$) are introduced into 20 ml of water and 60 mmol (9.789 g) of acesulfame-H are added. After $CO_2$ formation has ended, a homogeneous solution is obtained. The acesulfame-zinc complex crystallizes out, after concentrating the solution, in the form of colorless crystals with 99% yield.

The acesulfame-zinc complex decomposes at 255° C.

The crystal structure of the acesulfame-zinc complex was established by X-ray structural analysis.

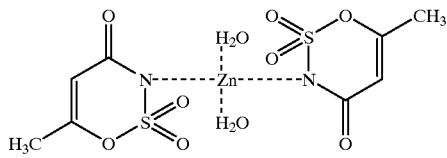

$(Ace)_2Zn$, $2C_4H_4NO_4S \cdot Zn \cdot 2H_2O$, $M_r=425.69$, monoclinic, C2/c, a=12.907(4), b=5.584(2), c=21.222(8) Å, β=91.31(3)°, V=1529.2(8) Å, Z=4, $D_x=1.849$ Mg m$^{-3}$, λ (Mo–Kα)= 0.71073 Å, $\mu=1.932$ mm$^{-1}$, F(000)=864, T=293(2) K, R=0.0235 and $R_W=0.0649$ for I>2δ(I) (1356 reflections), R=0.0255 and $R_W=0.0669$ for all 1436 unique CCD data. $\Sigma(F_o^2-F_c^2)^2$ was minimized.

EXAMPLE 2

Acesulfame-copper complex

Method 1

20 mmol (3.947 g) of sparingly soluble barium carbonate (or 20 mmol of calcium carbonate) are introduced into 20 ml of water and 40 mmol (6.525 g) of acesulfame-H are added. After $CO_2$ formation has ended, a homogeneous solution is obtained from which sparingly soluble barium sulfate (or calcium sulfate) is precipitated out by 20 mmol (0.499 g) of copper(II) sulfate pentahydrate. After filtering off the precipitate and concentrating the solution, the acesulfame-copper complex crystallizes out in the form of blue crystals with 96% yield.

Method 2

10 mmol (2.21 g) of sparingly soluble basic copper carbonate ($CuCO_3 \cdot Cu(OH)_2$) are introduced into 20 ml of water and 40 mmol (6.526 g) of acesulfame-H are added. After $CO_2$ formation has ended, a homogeneous blue solution is obtained. The acesulfame-copper complex crystallizes out in the form of blue crystals with 98% yield after concentrating the solution.

The blue acesulfame-copper complex decolorizes at 117° C. and decomposes at 179° C.

The crystal structure of the acesulfame-copper complex was established by X-ray structural analysis.

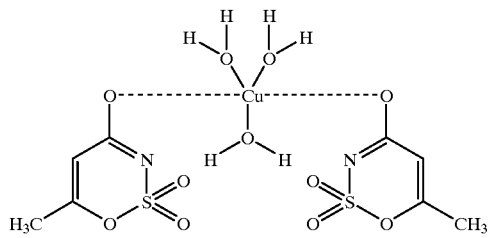

$(Ace)_2Cu$, $2C_4H_4NO_4S \cdot Cu \cdot 3H_2O$, $M_r=441.87$, monoclinic, C2/c, a=19.30(2), b=9.677(9), c=9.007(8) Å, β=102.92(2)°, V=1640(3) Å$^3$, Z=4, $D_x=1.790$ Mg m$^{-3}$, λ (Mo–Kα)= 0.71073 Å, $\mu=1.645$ mm$^{-1}$, F(000)=900, T=293(2) K, R=0.0371 and $R_W=0.0753$ for I>2δ(I) (1251 reflections), R=0.0440 and $R_W=0.0791$ for all 1448 unique CCD data. $\Sigma(F_o^2-F_c^2)^2$ was minimized.

The other acesulfame-trace element metal complexes, for example manganese-acesulfame, cobalt-acesulfame and iron-acesulfame complexes, may be prepared in a similar manner.

I claim:

1. A compound of a trace element wherein the trace element is zinc, copper, iron, manganese or cobalt and acesulfame with or without water of crystallization.

2. A compound as claimed on claim 1 wherein the trace element is a metal and and wherein the stoichiometry metal:acesulfame is equal to 1:2.

3. A compound as claimed in claim 1 characterized in that it is an ionic compound.

4. A process for preparing a compound as claimed in claim 1
   a) by reacting an acesulfame salt which is dissolved in a suitable solvent with a trace element wherein the trace element is zinc, copper, iron, manganese or cobalt salt which is also dissolved in this solvent, the cation of the acesulfame salt forming a compound with the anion of the trace element salt, which compound precipitates in this solvent, separating off this precipitates from the acesulfame-metal complex which remains in solution and then isolating this complex, or
   b) by reacting a carbonate, of the trace element wherein the trace element is zinc, copper, iron, manganese or cobalt with acesulfamic acid in a suitable solvent and then isolating the acesulfame-metal complex formed.

5. The process as claimed in claim 4, wherein, in variant b) in the reaction step of a carbonate with acesulfamic acid, the carbonate is barium carbonate or calcium carbonate.

6. The process as claimed in claim 4, wherein the trace element salt is a sulfate.

7. The process as claimed in claim 4, wherein the solvent is water or a water-miscible solvent or water and a water-miscible solvent.

8. Method of manufacturing a sweetner by incorporating a compound according to claim 1 into a sweetner.

9. Method of manufacturing a food supplement by incorporating a compound according to claim 1 into a food supplement.

10. Method of manufacturing a food additive by incorporating a compound according to claim 1 into a food additive.

11. Method of manufacturing a medicament additive by incorporating a compound according to claim 1 into a medicament additive.

12. Method of manufacturing a feed additive by incorporating a compound according to claim 1 into a feed additive.

13. Method of manufacturing an additive for cosmetic composition by incorporating a compound according to claim 1 into an additive for cosmetic composition.

14. A preparation comprising a compound as claimed in one or more of claim 1 and a chewing gum raw material, tablet raw material, granule raw material, compressed composition raw material or a premix raw material.

\* \* \* \* \*